US009113817B2

(12) United States Patent
Tripathi

(10) Patent No.: US 9,113,817 B2
(45) Date of Patent: Aug. 25, 2015

(54) SYSTEM FOR LOCATING ANATOMICAL OBJECTS IN ULTRASOUND IMAGING

(75) Inventor: Gaurav Tripathi, Lucknow (IN)

(73) Assignee: Siemens Medical Solutions USA, Inc., Malvern, PA (US)

( * ) Notice: Subject to any disclaimer, the term of this patent is extended or adjusted under 35 U.S.C. 154(b) by 582 days.

(21) Appl. No.: 13/153,726

(22) Filed: Jun. 6, 2011

(65) Prior Publication Data

US 2012/0101388 A1    Apr. 26, 2012

Related U.S. Application Data

(60) Provisional application No. 61/394,793, filed on Oct. 20, 2010.

(51) Int. Cl.
*A61B 8/00* (2006.01)
*A61B 8/08* (2006.01)

(52) U.S. Cl.
CPC ............. *A61B 8/085* (2013.01); *A61B 8/4254* (2013.01); *A61B 8/4263* (2013.01)

(58) Field of Classification Search
USPC .................. 600/407, 437–464, 472
See application file for complete search history.

(56) References Cited

U.S. PATENT DOCUMENTS

| 2004/0034301 | A1* | 2/2004 | Falco ............................ 600/427 |
| 2004/0167402 | A1* | 8/2004 | Jones et al. ................... 600/437 |
| 2005/0101868 | A1* | 5/2005 | Ridley et al. ................. 600/459 |
| 2006/0241405 | A1* | 10/2006 | Leitner et al. ................. 600/426 |
| 2007/0273504 | A1 | 11/2007 | Tran |

OTHER PUBLICATIONS

Wikipedia, The Free Encyclopedia, "3D ultrasound", http://en.wikipedia.org/wiki/3D_untrasound, website, printed May 25, 2011.
Wikipedia, The Free Encyclopedia, "Plane (geometry)", http://en.wikipedia.org/wiki/Plane_(geometry), printed May 25, 2011.

* cited by examiner

*Primary Examiner* — Mark Remaly

(57) ABSTRACT

An ultrasound imaging probe supports determination of the location of an object scanned within a 3D volume. A handheld movable ultrasound imaging device emits ultrasound waves and detects corresponding ultrasound waves reflected from an object. At least three light emitting elements are mounted on the ultrasound imaging device and are detectable by a camera located at a fixed position with respect to a 3D volume where the object is imaged. A motion detector provides data indicating detected movement of the ultrasound imaging device in at least one axis. The data indicating detected movement is used together with distance data indicating distance of the ultrasound imaging device from the camera derived using the light emitting elements and the camera, to determine a location of the object scanned within a 3D volume using the ultrasound imaging device.

16 Claims, 15 Drawing Sheets

SYSTEM FOR LOCATING ANATOMICAL OBJECTS IN ULTRASOUND IMAGING

This is a non-provisional application of provisional application Ser. No. 61/394,793 filed Oct. 20, 2010, by G. Tripathi.

FIELD OF THE INVENTION

This invention concerns an ultrasound imaging device supporting determination of the location of an object scanned within a 3D volume by detecting movement of the object using the ultrasound imaging device and distance of the ultrasound imaging device from a camera derived using the camera and light emitting elements on the device.

BACKGROUND OF THE INVENTION

It is difficult to locate and observe anatomy of an object in a three dimensional (3D) volume through ultrasound waves. The problem becomes more significant when the object scanned is a body organ which reflects specific waves and the anatomy of the object needs to be determined by scanning all around it. A single view of imaging data populated using ultrasound gives a view of the object with reference to a position at which the technician performed the scan and placed the probe. The difficulty in locating and observing anatomy of an object in a 3D volume derives from the fact that a transmitter-detector assembly needs to be continuously moved (often in close proximity) of the object to obtain the reflection of the waves from its different surfaces. It is not possible to map the data captured from each view to one composite view of the object in the 3D space using the imaging system.

Known 3D ultrasound systems are used for fetal scanning. In 3D fetal scanning, instead of sound waves being directed straight down and reflected back, they are sent at different angles. The returning echoes are processed by a sophisticated computer program resulting in a reconstructed three dimensional volume image of a fetus surface or internal organs, in much the same way as a CT scan machine constructs a CT scan image from multiple X-rays. 3D ultrasound scans provide width, height and depth of images in much the same way as 3D movies but no movement is shown. Moreover the data obtained by 3D fetal scanning cannot be mapped for locating the fetal position inside a 3D volume. A system according to invention principles addresses these deficiencies and related problems.

SUMMARY OF THE INVENTION

A system captures ultrasound data from multiple different views and maps the data to one composite view of a 3D object under scan and advantageously distinguishes the target organ from its surrounding organs in response to transmitted ultrasound waves. An ultrasound imaging probe supports determination of the location of an object scanned within a 3D volume. A handheld movable ultrasound imaging device emits ultrasound waves and detects corresponding ultrasound waves reflected from an object. At least three light emitting elements are mounted on the ultrasound imaging device and are detectable by a camera located at a fixed position with respect to a 3D volume where the object is imaged. A motion detector provides data indicating detected movement of the ultrasound imaging device in at least one axis. The data indicating detected movement is used together with distance data indicating distance of the ultrasound imaging device from the camera derived using the light emitting elements and the camera, to determine a location of the object scanned within a 3D volume using the ultrasound imaging device.

DETAILED DESCRIPTION OF THE INVENTION

A system captures ultrasound image data from multiple different views and maps the data to one composite view of a three dimensional (3D) object under scan. This advantageously distinguishes a target organ from surrounding organs in response to the ultrasound waves sent. During a contrast enhanced ultrasound scan the system facilitates understanding anatomical and physiological behavior of the organs and object. The system uses an ultrasound device which can be hand held by a technician or physician and moved over a patient body for scanning.

Figure 1:
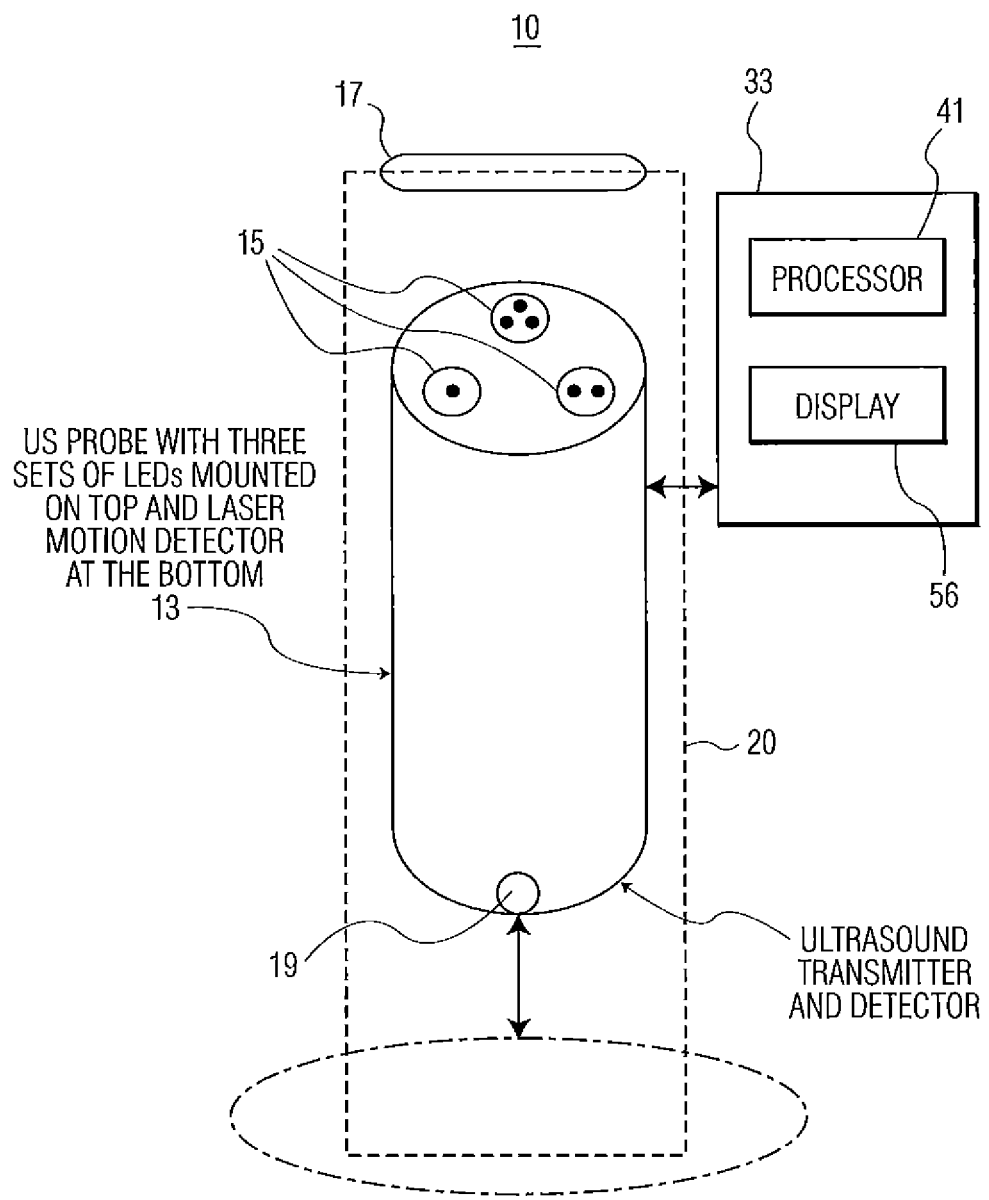
FIG. 1 shows an ultrasound imaging system supporting determination of the location of an object scanned within a 3D volume, according to invention principles.

FIG. 1 shows ultrasound imaging system 10 supporting determination of the location of an object scanned within a 3D volume. System 10 advantageously uses ultrasound probe 13 having, in one embodiment, three distinguishable light sources such as LEDs 15 on top of the ultrasound probe and motion detector 19 on the bottom of the probe. LEDs 15 are located at points A, B and C making an equilateral triangle, for example. The LEDs at points A, B and C are fitted in a position on probe 13 so that distance measured from ultrasound probe 13 to an anatomical object within a patient is mapped to the plane represented by these points and the points facilitate determining location and orientation of probe 13 in reference volume 20. Camera 17 with a known focal length is fitted above a patient support table. Camera 17 continuously captures images of LEDs 15 and the images are processed by computer system 33 to locate the movement of points A, B, C 15 and therefore of ultrasound probe 13. Movement detector (e.g., laser) 19 is attached to a point on probe 13 which comes in contact with patient anatomy. In one embodiment, detector 19 is similar to a laser commonly found in a mouse and which detects movement relative to a surface in close proximity to a mouse.

Figure 4:
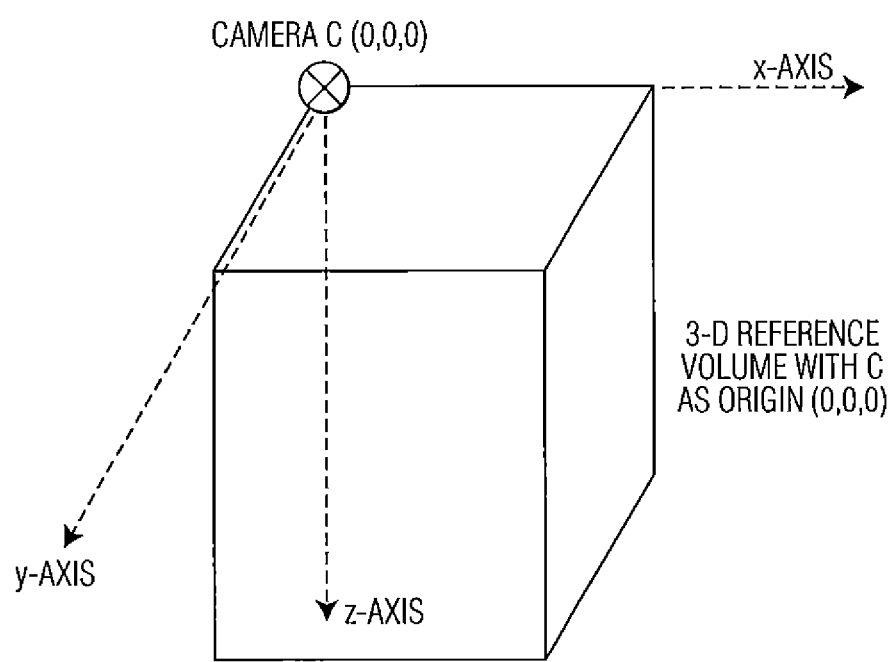
FIG. 4 shows a reference frame used in determination of the location of an object scanned within a 3D volume in a system, according to invention principles.

Handheld movable ultrasound imaging device 13 emits ultrasound waves and detects corresponding ultrasound waves reflected from an object. At least three light emitting elements 15 are mounted on the ultrasound imaging device. Camera 17 is located at a fixed position with respect to 3D (three dimensional) volume 20 where the object is imaged and detects light from the at least three light emitting elements 15 for tracking movement of the light emitting elements. Motion detector 19 provides data indicating detected movement of ultrasound imaging device 13 in at least one axis. At least one processor 41 in computer 33 processes the data indicating detected movement and distance data indicating distance of ultrasound imaging device 13 from camera 17 derived using light emitting elements 15 and camera 17, to determine a location of the object scanned within 3D volume 20 using ultrasound imaging device 13. FIG. 4 shows a reference frame and 3D coordinate system used in determination of the location of an object scanned within 3D volume 20. Display 56 presents a graphical user interface (GUI) for operation of system 10 and presents ultrasound images and associated data and measurements for viewing by a user.

Figure 2:
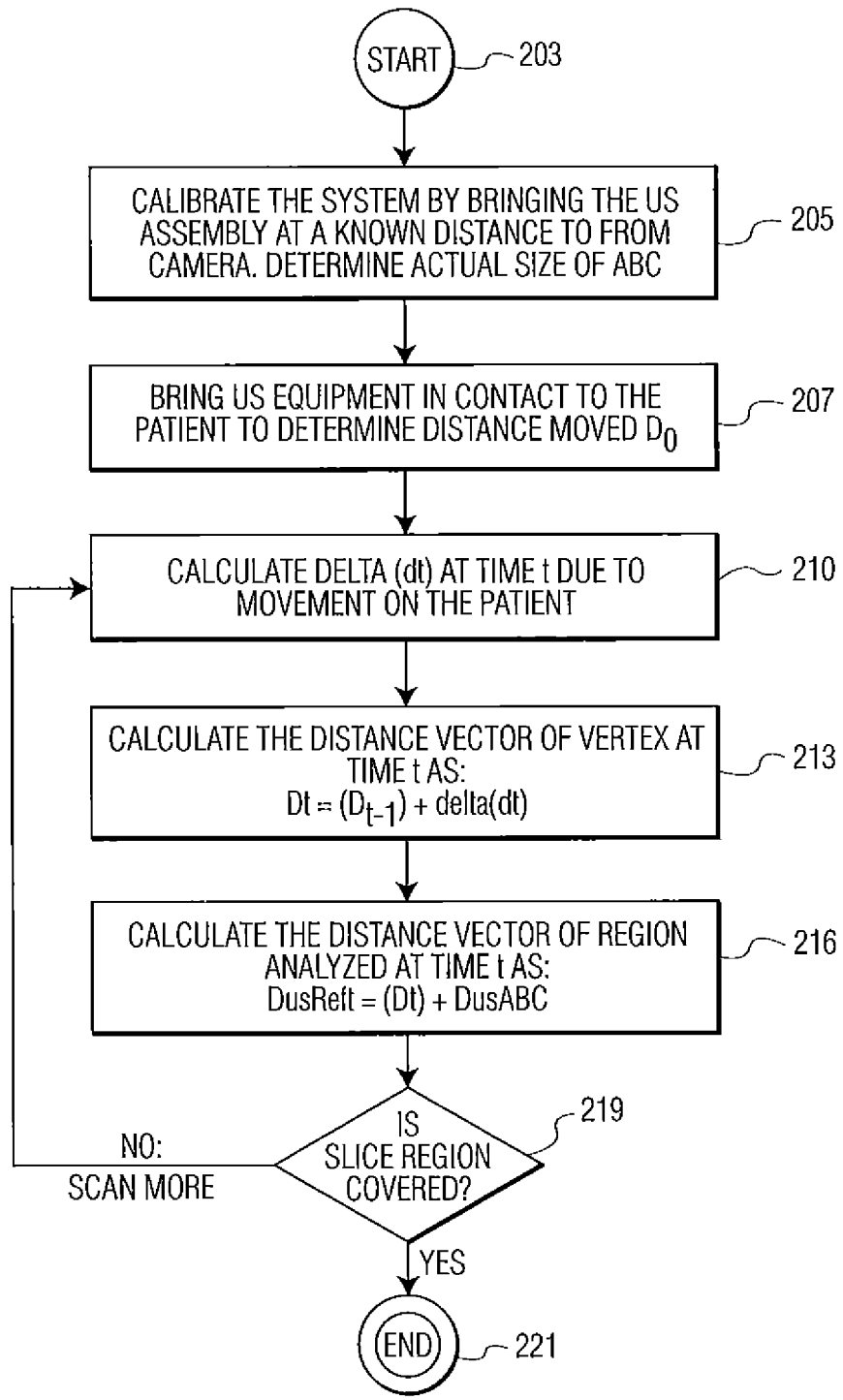
FIG. 2 shows a flowchart of a process used by an ultrasound imaging system supporting determination of the location of an object scanned within a 3D volume, according to invention principles.
Figure 5:
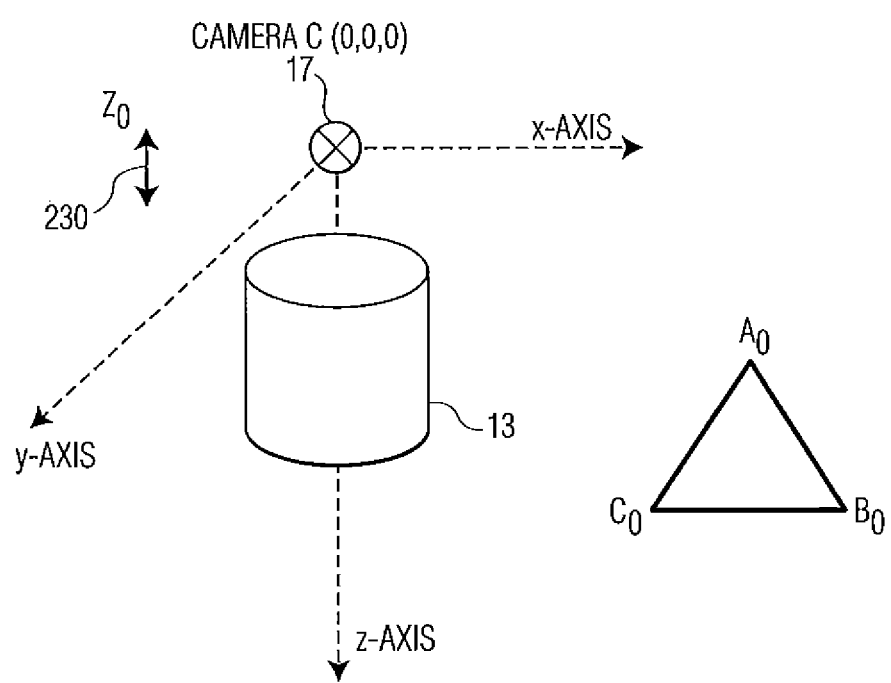
FIG. 5 illustrates probe size calculation used in determination of the location of an object scanned within a 3D volume in a system, according to invention principles.

FIG. 2 shows a flowchart of a process used by an ultrasound imaging system supporting determination of the location of an object scanned within a 3D volume. In step 205 following the start at step 203, in order to initialize system 10 (FIG. 1), ultrasound probe 13 is placed at a known distance from camera 17 and processor 41 determines an accurate size of a triangle formed by LEDs A, B and C 15. FIG. 5 illustrates probe size calculation used in determination of the location of an object scanned within a 3D volume in a system. Processor 41 determines size of triangle $A_0B_0C_0$ from image data acquired by camera 17 in response to probe 13 being brought to known distance $Z_0$ 230 from camera 17. The location of the target object in the 3d reference volume is performed by determining a reference position of the ultrasound device 13. A user brings LEDs A, B and C 15, mounted on top of the ultrasound device, to a point which is at a known distance from camera 17. Processor 41 calculates size of triangle ABC drawn on the ultrasound probe using, $$\frac{\text{Focal Length} \times \text{Object size}}{\text{Lens-to-object distance}} = \text{Image Size}$$

Figure 3:
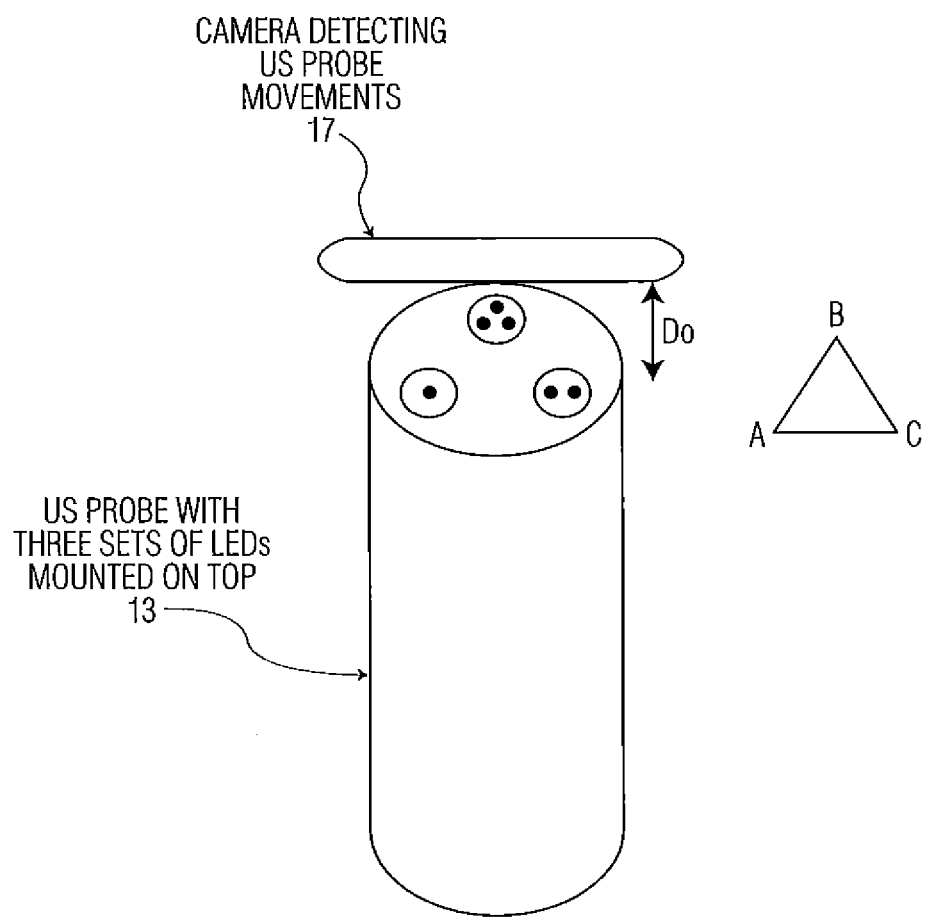
FIG. 3 shows an initial step in determination of the location of an object scanned within a 3D volume in a system, according to invention principles.
Figure 6:
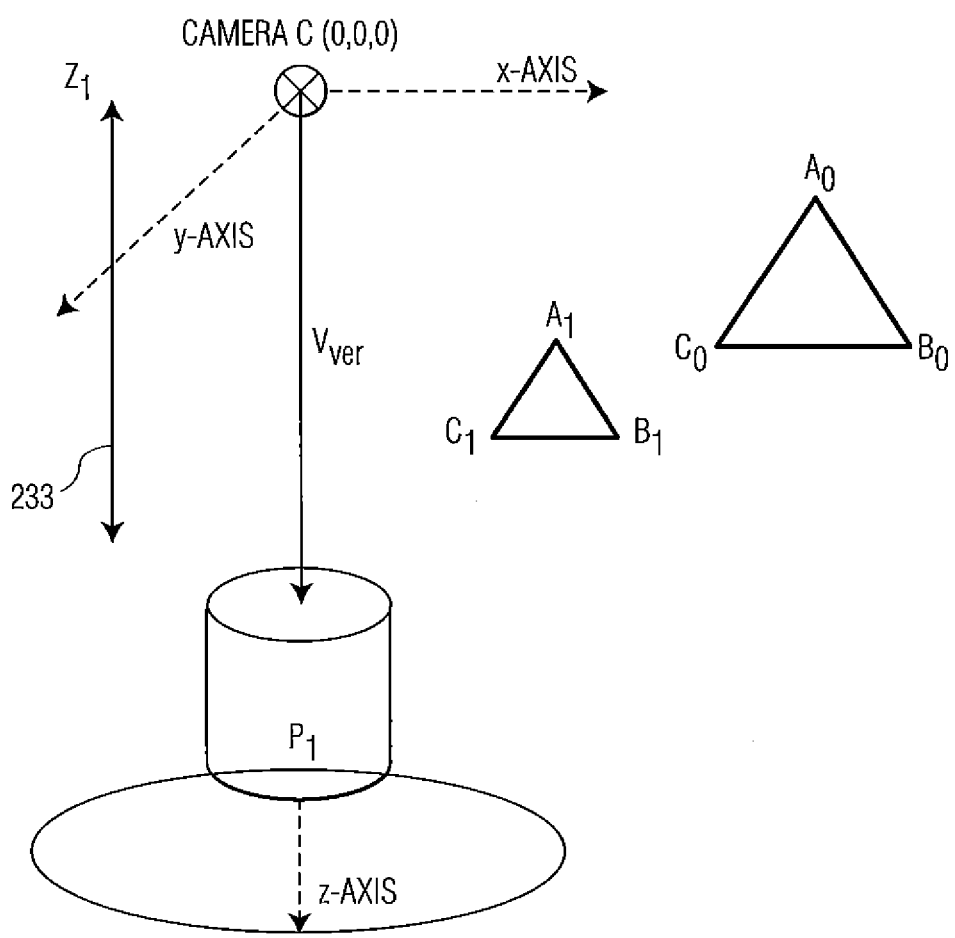
FIG. 6 illustrates calculation of vertical probe displacement used in determination of the location of an object scanned within a 3D volume in a system, according to invention principles.
Figure 10:
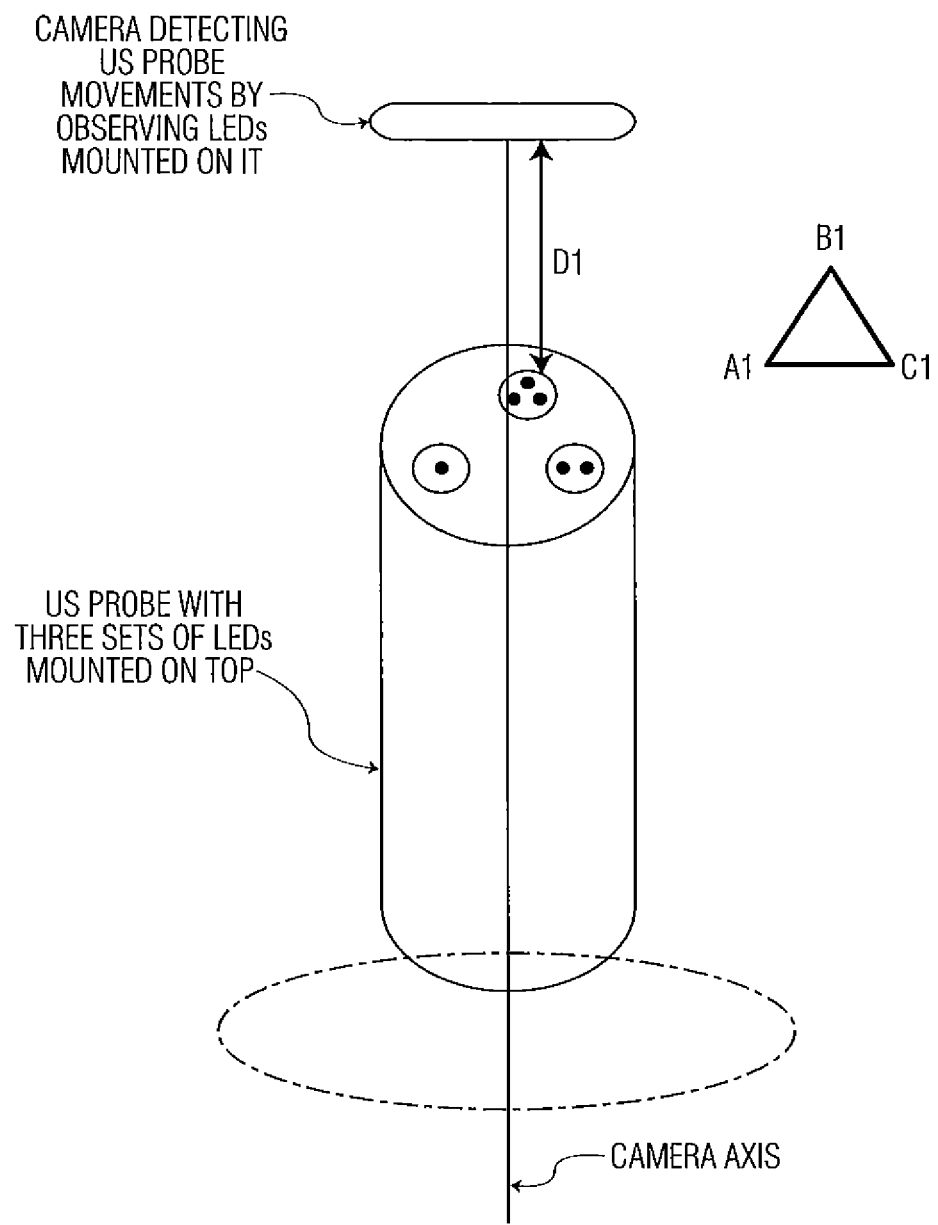
FIG. 10 illustrates calculating vertical movements of a hand held ultrasound device, according to invention principles.

In step 207, processor 41 determines a distance moved by probe 13 $D_0$, in response to probe 13 being brought in contact with patient anatomy. FIG. 6 illustrates calculation of vertical probe displacement used in determination of the location of an object scanned within a 3D volume in system 10. Processor 41 determines the magnification of $A_1B_1C_1$ with respect to $A_0B_0C_0$ using image data acquired by camera 17. LED triangle $A_1B_1C_1$ is shown in an image acquired by camera 17 at an unknown distance $Z_1$ 233 from the origin at camera 17, when probe 13 touches patient point $P_1$ (at time t=0). Processor 41 uses a determined magnification factor to derive displacement $Z_1$ 233 of probe 13 along the Z-axis upon the probe touching patient $P_1$. Hence processor 41 determines vertical vector $V_{ver}=(0, 0, Z_1)$. FIG. 3 shows determination of vertical distance of each LED at time t using the previously described image size function, AB is actual length of side AB of the triangle as calculated, AtBt is the length of side AB of triangle as seen at time t from vertical distance Dt. The location of centre of the triangle ABC at any point t is calculated as D0. FIG. 10 illustrates calculating vertical movements of hand held ultrasound device 13. Handheld ultrasound device 13 is moved along the axis of the lens, until it touches the patient body at the point where the examination is to be done. System 10 continues to capture images of LEDs and at any time t, from the images obtains a new triangle $A_1B_1C_1$.

Figure 7:
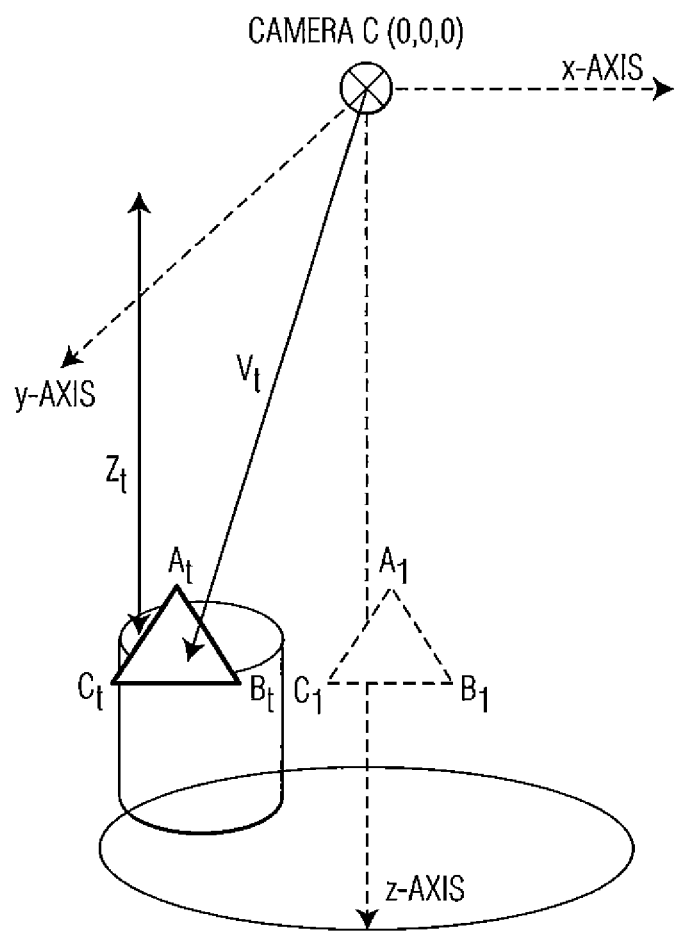
FIG. 7 illustrates motion calculation used in determination of the location of an object scanned within a 3D volume in a system, according to invention principles.
Figure 11:
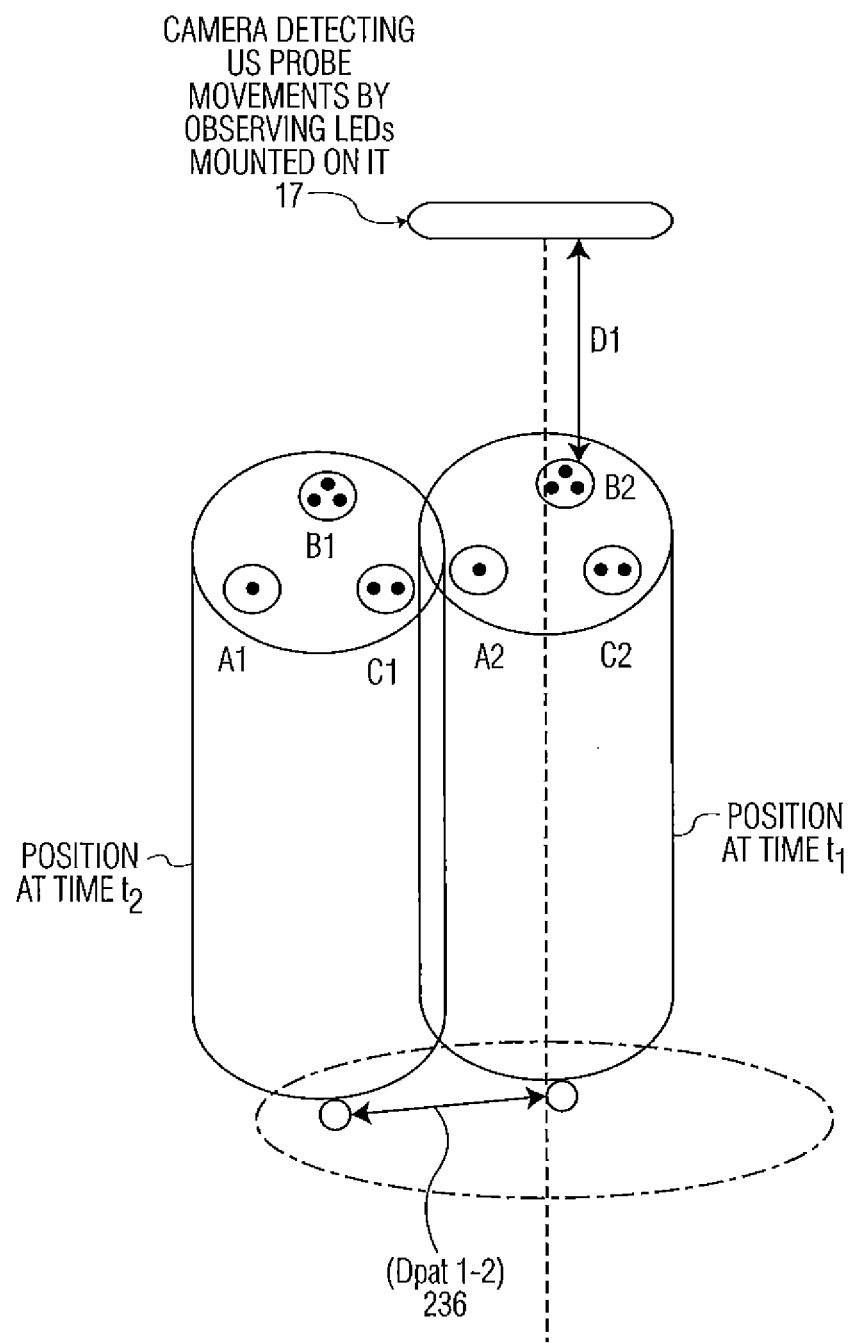
FIG. 11 illustrates probe movement calculation used in determination of the location of an object scanned within a 3D volume in a system, according to invention principles.

In step 210 (FIG. 2), processor 41 determines a distance delta (dt) moved by a center point (a vertex of the 3 medians of a triangle) between LED triangle positions $A_1B_1C_1$ and $A_2B_2C_2$ of probe 13 as determined by motion detector 19 as illustrated in FIG. 11. Specifically, FIG. 11 illustrates probe 13 movement of distance $Dpat_{1-2}$ 236 in the camera axis as the probe is moved across patient anatomy between times t1 and t2 (of time difference dt). FIG. 7 similarly shows movement of the LED triangle center point between LED triangle positions $A_1B_1C_1$ and $A_tB_tC_t$ of probe 13 as determined by motion detector 19. LEDs form triangle $A_tB_tC_t$ at a point in time t at distance $Z_t$ from the origin. The magnification in image of $A_tB_tC_t$ with respect to the triangle $A_0B_0C_0$ determined at the calibration position (previously shown in FIG. 6) gives the displacement of probe $Z_t$ along the Z-axis. The shift of the center point of the triangle along the x-y plane, i.e. $(X_t, Y_t)$ is determined by the shift in coordinates of center point at time t. Hence the location of the triangle center point at time t in reference volume 20 is determined by the vector $V_t=(X_t, Y_t, Z_t)$ In step 213, processor 41 calculates a distance vector of the LED triangle center point at time t as, $$D_t=D_{t-1}+\text{delta}(dt)$$

Where delta (dt) is distance moved by the center point at time t from initial distance $D_{t-1}$ at prior time$_{t-1}$.

Figure 8:
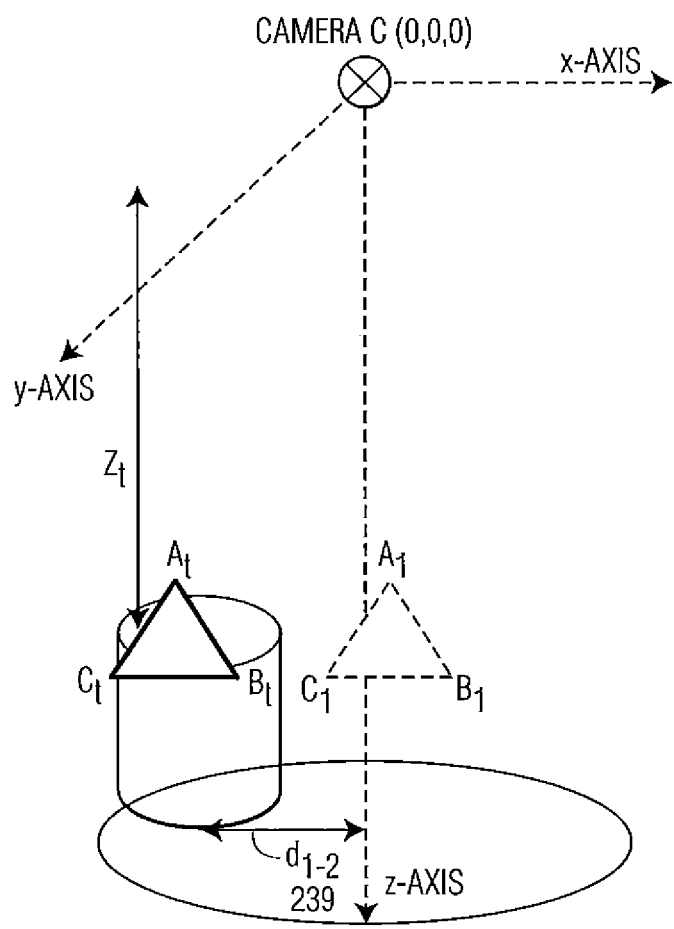
FIG. 8 illustrates movement calculation of an ultrasound probe where orientation of the probe is unchanged, according to invention principles.

FIG. 8 illustrates movement calculation of probe 13 where orientation of probe 13 is unchanged. Distance $(d_{1-2}$ 239 moved by the probe from time $t_1$ to $t_2$ is determined by subtraction of vectors representing the LED triangle $A_1B_1C_1$ and $A_tB_tC_t$ center points at these times, $$d_{1-2}=((X_1-X_2)^2+(Y_1-Y_2)^2+(Z_1-Z_2)^2)^{1/2}$$

Figure 9:
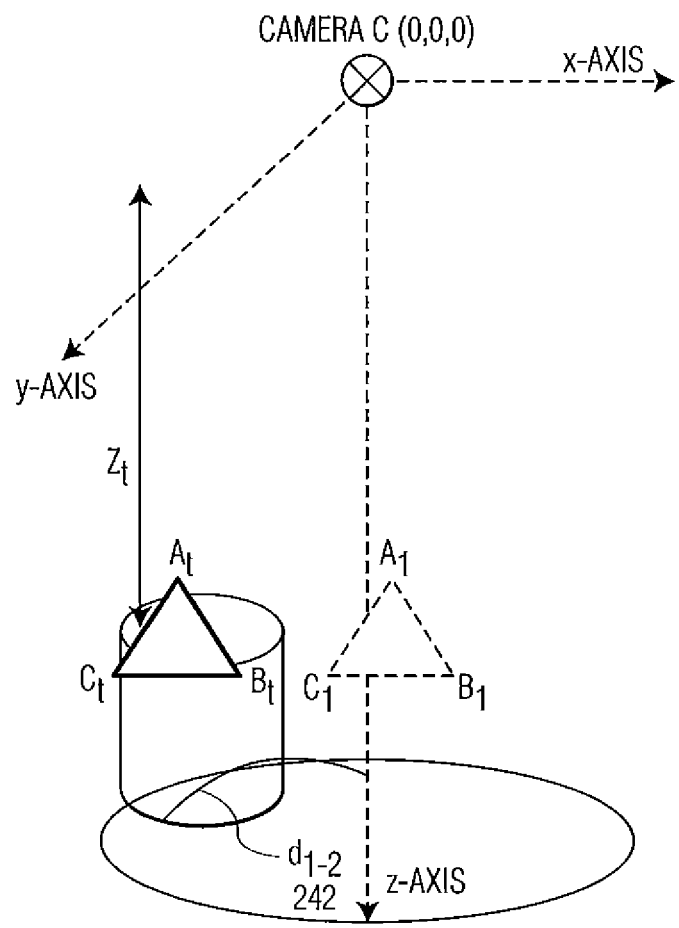
FIG. 9 illustrates movement calculation for correction for non-axial movement of an ultrasound (US) device where orientation of the device is changed, according to invention principles.

FIG. 9 illustrates movement calculation for correction for non-axial movement of the ultrasound (US) device 13 where orientation of probe 13 is changed. Processor 41 determines how far probe 13 is moved from the line of sight axis through camera 17 by position of the three LED triangle ABC points along with the movement data captured by the movement detector 19. Distance $d_{1-2}$ 242 changes when the orientation of LED triangle ABC is changed as probe 13 is moved on a patient. This is because upon change of orientation, points A, B and C are not lying on a plane perpendicular to camera 17 line of sight axis. Processor 41 compares distance $d_{1-2}$ 242 as measured in FIG. 8 with distance $d_{1-2}$ 242 determined using motion detector 19 fitted at the base of probe 13. If there is a difference, processor 41 corrects distance $d_{1-2}$ 242 with movement data determined using motion detector 19. Specifically, processor 41 corrects displacement measurement due to change in orientation of probe 13. For example, in determination of location of probe 13 at time t=1, if a 3D coordinate vector representing the center point of triangle ABC is given by, $V_1$=(0 cm, 0 cm, 10 cm) and motion detector 19 detects distance moved on a patient at time t=1 as, 2 cm along x and 1 cm along y axis, processor 41 corrects the resultant location of point at time t=1 to be $V_r$=(2 cm, 1 cm, 10 cm).

Figure 12:
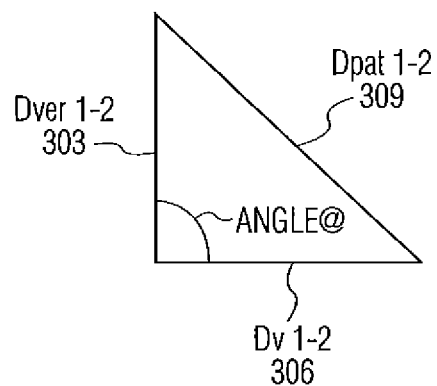
FIG. 12 illustrates movement calculation for correction for non-axial movement of the ultrasound (US) device using both detected LED triangle location data and motion detector data, according to invention principles.

FIG. 12 illustrates movement calculation for correction for non-axial movement of the ultrasound (US) device 13 using both LED triangle and motion detector 19 data. Processor 41 determines vertical distance moved by probe 13 (Dver1-2 303) using a right angle triangle estimation comprising Dver1-2 303, Dv1-2 306 and Dpat1-2 309, where Dv1-2 306 comprises distance moved by the center point of triangle ABC as calculated in step 213 and Dpat1-2 309 comprises distance moved by probe 13 on the patient as captured by motion detector 19. In the calculation, for a short time where t2–t1 tends towards zero, Dpat1-2 comprises a straight line. Hence the vertical movement of the ultrasound assembly is calculated by processor 41 using right angle triangle properties.

Figure 13:
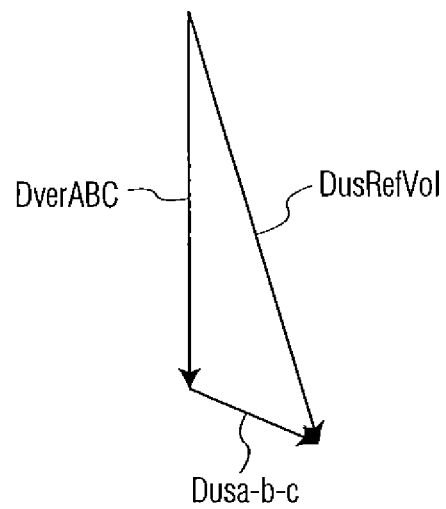
FIG. 13 illustrates a vector calculation in determination of the location of an object scanned within a 3D volume in a system, according to invention principles.

In step 216, processor 41 performs a vector calculation to determine location of an object inside reference volume 20 (FIG. 1). In response to three dimensional location of the LED triangle points of probe 13 in steps 205-213, the location of an anatomical object in volume 20 is determined. FIG. 13 illustrates a vector calculation in determination of the location of an object scanned within 3D volume 20. Specifically, processor 41 calculates a resultant distance vector (DusRefVol) of an object in volume 20 as, $$\text{Vector}(\text{DusRefVol}) = \text{Vector}(\text{Dus}_{a-b-c}) + \text{Vector}(\text{Dver}_{a-b-c})$$

Where, $\text{Dus}_{a-b-c}$=a distance vector calculated by ultrasound system 10 (FIG. 1) and probe 13 of a target object (using reflected ultrasound waves) within patient anatomy and volume 20 with respect to the center point of triangle ABC as captured by the ultrasound probe 13 with respect to the plane on which points ABC lie and Dvera-b-c=distance vector of the center point of triangle ABC with respect to 3D volume 20 as calculated in step 213 (FIG. 2). The vertical component of vector DusRefVol provides a distance of each point of a target anatomical object comprising vertical locations of each pixel from a plane where camera 17 is placed.

Figure 14:
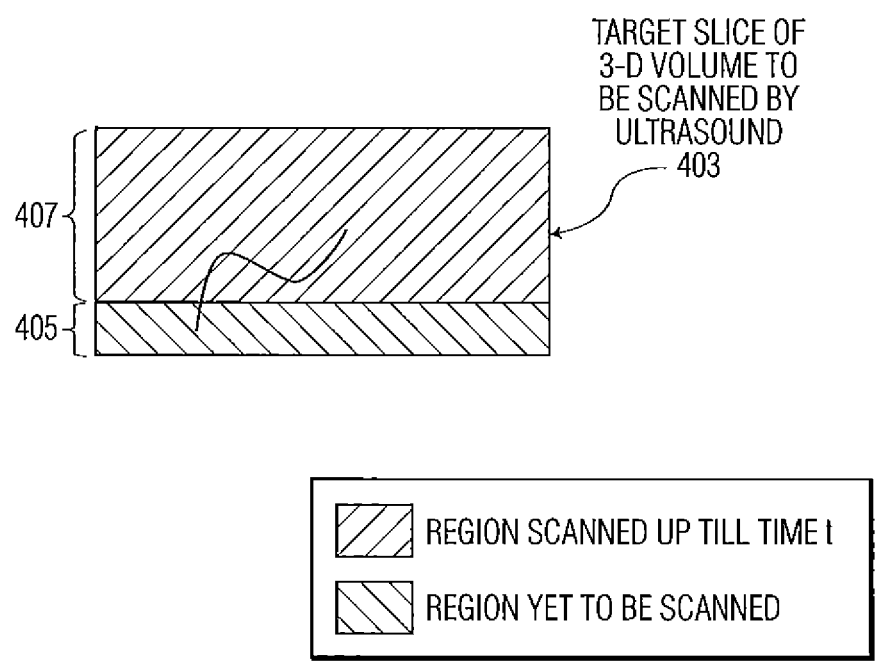
FIG. 14 shows a display image guiding a user in ultrasound scanning a region of interest (ROT) according to invention principles.

In step 219, processor 41 determines whether an imaging slice region within reference volume 20 (FIG. 1) has been imaged and processed. Processor 41 processes data indicating movement of LED triangle ABC points and determines the section of a volume 20 slice scanned by ultrasound device 13 at a time t. This information assists a user in scanning a targeted portion of a slice of 3D volume 20 and directs a user to scan in a particular direction and also to stop scanning if probe 13 is being moved out of volume 20. FIG. 14 shows a display image guiding a user in ultrasound scanning a ROI. Processor 41 uses the calculated distance and vector data in determining that region 405 of slice 403 is already scanned and region 407 is yet to be scanned. Processor 41 provides a graphical representation of progress of scanning showing slice 403 and regions 405 and 407 for use in guiding a user in moving probe 13 to complete scanning of slice 403. The process of FIG. 2 terminates at step 221.

Figure 15:
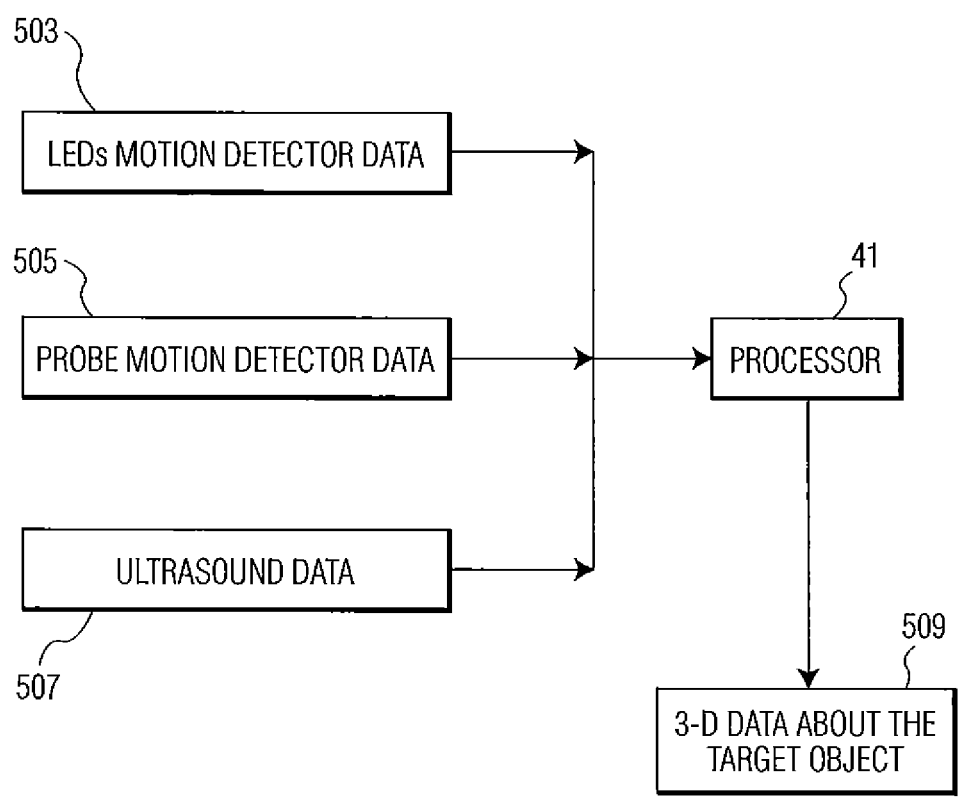
FIG. 15 shows data flow used in determination of the location of an object scanned within a 3D volume in a system, according to invention principles.

FIG. 15 shows data flow in determination of the location of an object scanned within 3D volume 20 in system 10 (FIG. 1). Processor 41 acquires ultrasound imaging data 507 from handheld movable ultrasound imaging device 13 indicating distance of an anatomical object from probe 13, data 505 indicating detected movement of ultrasound imaging device 13 in at least one axis from motion detector 19 and movement data 503 derived using camera 17 indicating movement of at least three light emitting elements mounted on ultrasound imaging device 13. Processor 41 processes acquired data, 503, 505 and 507 to calculate a resultant distance vector 509 of an object in volume 20 and provide a graphical representation of progress of scanning showing a slice for use in guiding a user in moving probe 13 to complete scanning of the slice.

Increasing the size of LED triangle ABC on ultrasound assembly probe 13 improves accuracy of detection of probe 13 movement. Also scanning is performed in such a way that the orientation of triangle ABC is visible and accurately detected by camera 17. System 10 advantageously integrates data captured through ultrasound scanning performed in close proximity of a target anatomical object at different time instances and associates that data with a 3D volume where the target object is located. The system supports real time observation and user performance of an imaging scan and detects movement of probe 13 in a 3D volume and makes measurement based on reflective rays compatible with other radiation imaging systems (transmitting or absorption radiations).

In another embodiment, instead of using LEDs, an ultrasound assembly is mounted with radio frequency transmitter/receiver, to detect movements to an acceptable accuracy. Movement of points A, B and C on the probe may also be detected by placing a laser emitter/detector that can detect the movement of reflecting points on the patient. An additional LED may be placed at the vertex of triangle ABC, to help in identifying the orientation of the assembly if the ultrasound is held at a position where the plane ABC is not perpendicular to axis of the camera lens.

Figure 16:
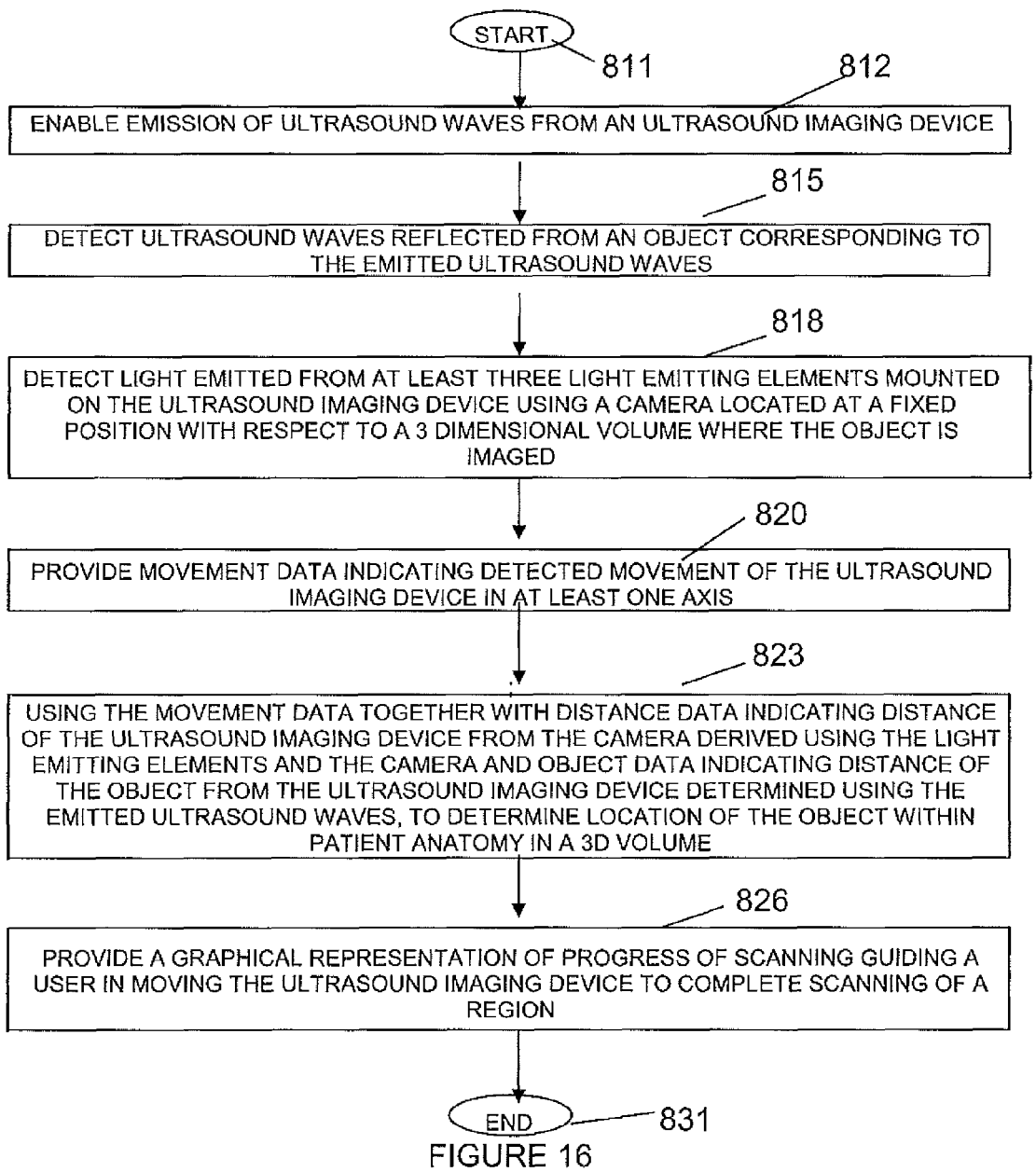
FIG. 16 shows a flowchart of a process used by an ultrasound imaging system supporting determination of the location of an object scanned within a 3D volume, according to invention principles.

FIG. 16 shows a flowchart of a process used by ultrasound imaging system 10 (FIG. 1) supporting determination of the location of an object scanned within 3D volume 20. In step 812 following the start at step 811, ultrasound imaging probe 13 enables emission of ultrasound waves. In step 815, probe 13 detects ultrasound waves reflected from an object corresponding to the emitted ultrasound waves. In step 818, camera 17 located at a fixed position with respect to three dimensional volume 20 where the object is imaged, detects light emitted from at least three light emitting elements 15 mounted on ultrasound imaging device 13. Camera 17 continuously periodically acquires images of the light emitting elements to track movement of the light emitting elements. Light emitting elements 15 lie in a plane having a known orientation with respect to direction of ultrasound wave emission by ultrasound imaging devices 15. Light emitting elements 15 are individually distinguishable from each other by image data derived by the camera and comprise at least one of, (a) LEDs and (b) light reflective elements. Movement detector 19 provides movement data indicating detected movement of ultrasound imaging device 13 in at least one axis. The detected movement of the ultrasound imaging device is used to correct for movement of the ultrasound imaging device away from an axis parallel to direction of ultrasound wave emission.

Processor 41 in step 823 uses the movement data together with distance data indicating distance of ultrasound imaging device 13 from camera 17 derived using light emitting elements 15 and camera 17 and object data indicating distance of the object from ultrasound imaging device 13 determined using the emitted ultrasound waves, to determine a location of the object scanned within patient anatomy in 3D volume 20 with respect to camera 17 using ultrasound imaging device 13. Processor 41 determines the distance data indicating distance of the ultrasound imaging device from the camera by geometrically processing image data acquired by the camera identifying relative location of the individual elements of the light emitting elements. In step 826, processor 41 also uses the movement data, distance data and object data to provide a graphical representation of progress of scanning guiding a user in moving the ultrasound imaging device to complete scanning of a region (e.g., a slice.). The process of FIG. 16 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-16 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. An ultrasound imaging system determines the location of an object scanned within a 3D volume by capturing ultrasound image data from multiple different views and maps the data to one composite view of a three dimensional (3D) object under scan. Further, the processes and applications may, in alternative embodiments, be located on one or more (e.g., distributed) processing devices on a network linking the units of FIG. 1. Any of the functions and steps provided in FIGS. 1-16 may be implemented in hardware, software or a combination of both.

What is claimed is:

1. An ultrasound imaging system configured to determine a location of a scanned object in a three dimensional (3D) volume having an x-axis, a y-axis and a z-axis, comprising:
    an ultrasound probe configured to acquire ultrasound imaging data by emitting ultrasound waves and detecting corresponding ultrasound waves reflected from the scanned object;
    a plurality of distinguishable light sources disposed on a top surface of the ultrasound probe, the light sources configured relative to each other to form a shape;
    a motion detector configured to acquire motion data indicating motion of the ultrasound probe along at least one of the x-axis, the y-axis and the z-axis;
    a camera in a fixed position configured to acquire a plurality of images, each image having image data comprising at least the plurality of light sources; and
    a processor configured to:
        receive the ultrasound imaging data;
        receive the image data in the plurality of images acquired by the camera;
        receive the motion data; and
        determine a location of the scanned object by: (i) determining a first displacement of the probe along the z-axis based on a change between a size of the shape in a first image and a size of the shape in a second image acquired after the first image; (ii) determining a second displacement of the probe along the x-axis, the y-axis or both the x-axis and the y-axis based on the motion data indicating a distance moved by the shape between two images acquired at different times.

2. The ultrasound imaging system of claim 1, wherein the plurality of distinguishable light sources comprises a plurality of light emitting diodes.

3. The ultrasound imaging system of claim 1, wherein the plurality of distinguishable light sources comprises at least three distinguishable light sources.

4. The ultrasound imaging system of claim 1, wherein the plurality of distinguishable light sources lie in a plane having a known orientation with respect to a direction of ultrasound wave emission by the ultrasound probe.

5. The ultrasound imaging system of claim 4, wherein the plurality of distinguishable light sources are configured in a triangle pattern.

6. The ultrasound imaging system of claim 1, wherein the plurality of distinguishable light sources comprises a plurality of light reflective elements.

7. The ultrasound imaging system of claim 1, wherein the motion detector comprises a laser motion detection device.

8. The ultrasound imaging system of claim 1, wherein the camera has a predetermined focal length and the processor determines the size of the shape in the first image based on the predetermined focal length and a predetermined distance between the probe and the camera at a time the first image is acquired.

9. The ultrasound imaging system of claim 1, wherein the processor further outputs a graphical representation to a user indicating scanning progress based on the location of the scanned object.

10. The ultrasound imaging system of claim 1, wherein determining a location of a scanned object further comprises determining a distance of the scanned object from the ultrasound probe.

11. The ultrasound imaging system of claim 10, wherein determining the distance of the scanned object from the ultrasound probe comprises geometrically processing the image data from the camera and identifying relative locations of each of the distinguishable light sources.

12. The ultrasound imaging system of claim 1, wherein the processor determines the change between the size of the shape in the second image and the size of the shape in the first image using a magnification factor.

13. The ultrasound imaging system of claim 1, wherein a distance moved by the shape between two images is a distance moved between a center point of the shape between two images.

14. The ultrasound imaging system of claim 1, wherein determining the second displacement of the probe along the x-axis, the y-axis or both the x-axis and the y-axis further comprises calculating distance vectors indicating the locations, at points along the x-axis, the y-axis and the z-axis, of the center of the shape in the two images acquired at the different times and subtracting the calculated distance vectors.

15. The ultrasound imaging system of claim 14, wherein the processor is further configured to correct for non-axial movement of the probe relative to the camera by changing the calculated distance vector to have the locations of the center of the shape along the x-axis, the y-axis or both the x-axis and the y-axis that are identified by the motion detector.

16. The ultrasound imaging system of claim 14, wherein the processor is further configured to determine a location of the scanned object by calculating a resultant distance vector indicating the location of the scanned object based on: (i) a distance vector of the scanned object in the 3D volume with respect to the shape using the ultrasound imaging data; and (ii) one of the calculated distance vectors indicating the location, at points along the x-axis, the y-axis and the z-axis, of the center of the shape in the corresponding image.

* * * * *